United States Patent [19]

Arkles et al.

[11] 4,078,971

[45] Mar. 14, 1978

[54] BOUND, ACTIVE CELLULAR ORGANELLES AND METHOD OF PRODUCING SAME

[75] Inventors: Barry Arkles, Oreland; William S. Brinigar, Bala Cynwyd, both of Pa.

[73] Assignee: Temple University, Philadelphia, Pa.

[21] Appl. No.: 672,483

[22] Filed: Mar. 31, 1976

[51] Int. Cl.$^2$ .................. C07G 7/022; C07G 7/026; C07G 7/028; C12K 9/00

[52] U.S. Cl. ........................................ 195/63; 195/1.8; 195/68; 195/DIG. 11; 424/95; 424/101

[58] Field of Search ........ 424/101; 195/1.8, DIG. 11, 195/63, 68

[56] References Cited

U.S. PATENT DOCUMENTS

| | | | |
|---|---|---|---|
| 3,553,310 | 1/1971 | Csizmas et al. | 424/2 |
| 3,652,761 | 3/1972 | Weetall | 424/12 |
| 3,836,433 | 9/1974 | Wirth et al. | 195/68 |
| 3,957,580 | 5/1976 | Nelson | 195/59 |

OTHER PUBLICATIONS

Lyttleton – Chem. Abst. vol. 74 (1971), p. 10,169 d.

Primary Examiner—Sam Rosen
Attorney, Agent, or Firm—Miller & Prestia

[57] ABSTRACT

Cellular organelles, examples of which are mitochondria, microsomes and chloroplasts, are bound in an active state on a substantially inert and insoluble support surface, examples of which are alkylated glass, kaolin, talc, silica, ferrites, alumina, and some alkyl substituted high molecular weight polymers. Binding between the support surface and the organelle is accomplished by adsorption of the isolated organelle onto the support surface. Immobilization in this manner does not affect the functional behavior of the organelle. These systems have utility for the synthesis of specific chemical substances.

13 Claims, 3 Drawing Figures

BOUND, ACTIVE CELLULAR ORGANELLES AND METHOD OF PRODUCING SAME

This invention pertains to biologically active cellular organelles bound on an inert substrate, to the method of producing such bound organelles, and to a method of producing desirable chemical substances using the bound organelles.

It is well known that enzymes, polypeptides of discrete composition, structure and topography, are effective in promoting or facilitating various chemical changes and transformations. The use of such materials in biologically mediated organic reactions has been recognized for centuries as a method of utility for the production of various foodstuffs and chemicals. Isolation of these enzymatic materials to permit them to be used more effectively has met with some success. However, the expense of isolation or synthetic preparation, the lability of typical enzymes and the difficulty in separating the enzyme from reaction media have until recent advances severely limited consideration of these systems for many commercial applications. Enzymes in the past few years have been immobilized on polymer and inorganic supports by several techniques including adsorption, inclusion, and covalent bonding. As described for example in U.S. Pat. No. 3,519,538 - Messing et al., the immobilized enzymes exhibit enhanced stability and may be employed in continuous packed columns or other types of chemical treatment equipment to promote specific chemical reactions.

In general, however, bound enzymes have been useful only in catabolic reactions, i.e. reactions in which complex materials are degraded into simpler ones. Moreover, many enzymes occur naturally as complexes either with other enzymes or membranes of distinct morphology. Very often these enzymes cannot be isolated from these complexes in an active form.

Biologically active cellular organelles, such as mitochondria and chloroplasts, are capable of generating reduced pyridine nucleotides and/or ATP intermediates in a variety of energy-requiring biological reactions. Mitochondria, microsomes and chloroplasts are characterized as membrane-bound cellular organelles because while they are enclosed by membranes, they are in fact constituents of and included within a variety of types of cells.

While conventional techniques are available for isolating these cellular organelles, the disposition of such materials in a form conducive to their use in chemical synthesis has not previously been achieved.

It is therefore a general object of the present invention to provide a method for producing biologically active cellular organelles bound to an inert solid support.

More specifically, it is an object of this invention to provide cellular organelles, such as chloroplasts, mitochondria and microsomes, in an active state on an inert support suitable for producing desired chemical substances in a continuous system.

These and other objects, which will be apparent in the course of the following description of this invention, are met by cellular organelles, examples of which are mitochondria, microsomes and chloroplasts, bound in an active state on a substantially inert and insoluble support, examples of which are alkylated glass, kaolin, talc, silica, ferrites, alumina, and some alkyl substituted high molecular weight polymers.

Bound cellular organelles may be produced as follows: An inert substrate, preferably of particle size 100-150 mesh, is preferably first treated with a hydrophobic coupling agent, such as an alkylsilane. The alkyl silane may be of the general structure $R_nSiX_{4-n}$ where $n = 1$ to 3, $x$ is halogen, alkoxy or some other labile substituent, and R is hydrocarbon of 2 to 24 carbon atoms. The alkylsilane is reacted with the surface of the inert support. Subsequent contact of the support with the cellular organelles, isolated first in a conventional manner and preferably after substantially all free lipid has been removed therefrom, results in what is believed to be a largely hydrophobic interaction between the organelles and the support surface which permits the organelles to be retained on the support in biologically active form.

This invention may be better understood by reference to the following detailed description thereof, taken in conjunction with the appended claims and the figures, in which:

Figure 1:
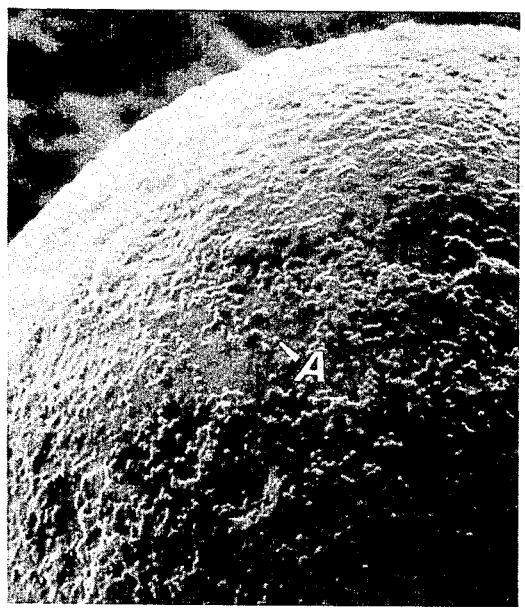
FIG. 1 is a scanning electron microphotograph, at a magnification of 1000x, of mitochondria (designated by reference letter A) bound on an alkylsilylated porous silica bead.

In producing these bound cellular organelles, the surface of the substantially inert and insoluble support may be treated with any of a variety of hydrophobic coupling agents. Particularly preferred are the alkylsilanes described above. Other coupling agents may be preferred for specific organelles. The organelles are prepared in the usual manner with special emphasis placed on the removal of excess lipid. When purified fractions of chloroplasts, microsomes or mitochondria are passed through packed beds of columns of alkylsilane treated inert support material, the organelles adhere to the solid phase. Based primarily on other known characteristics of the organelles and the cold lability of the bound organelles, the probable mechanism for the binding is that of hydrophobic interaction. Such an effect is described by Tanford in his work, "The Hydrophobic Effect" published by Wiley in 1973.

In general, the present invention provides a useful product and a method for producing that product. The bound organelles may be provided with a variety of reactive constituents to produce ATP, which in turn may be used in reactions analogous to those occurring in plants and animals to effect still other chemical reactions, particularly reactions involving the synthesis of complex molecules. Ultimately then such systems may be produced, for example, by using the present invention in a form in which biologically active cellular organelles are attached to the inner surface of glass tubes through which reactants in a fluid medium are passed. Exposure of such a system using chloroplasts to a light source such as the sun may result in the efficient utilization of light energy in the production of a complex product or some other energy-requiring intermediate product. Many reactions observed as natural biological phenomena may be utilized.

The invention has been substantially described in a publication by the inventors in the *Journal of Biological Chemistry*, published in November, 1975, which is incorporated herein by reference.

Following are several examples demonstrating the production of the product of the present invention using the method of the present invention and several additional examples demonstrating the use of the product of this invention in a process for the production of chemical substances. The production of these substances demonstrates the utility of the product of the present invention in the utilization of natural biological processes.

EXAMPLE I

An adult male Spraque-Dawley rat was decapitated and then exsanguinated. A ventral incision was made and all lobes of the liver were removed and placed immediately into ice cold 0.25 M sucrose containing 0.4 mM Tris buffered to pH 7.4. The liver was cut into small sections with a pair of scissors. The solution was decanted to remove debris and loose blood cells and immediately replaced with fresh solution. The liver was then homogenized with a Potter-Elvejhem tissue grinder while maintaining a 0° – 5° C temperature. The suspension was centrifuged for 10 minutes at 800xg to remove debris. The supernatant was swabbed to remove floating lipid and retained. It was then centrifuged for five minutes at 9000g. The pellet, mitochondria substantially free of excess lipid, was retained and resuspended in about 5 mls of 0.25 M sucrose.

In this example octadecylsilylated porous silica beads with an average diameter of 220 – 230 microns, a surface area of 50 – 200 $m^2$/mg and an average pore size of 200 – 400 A were employed as the inert substrate for the bound organelle. The silylation was accomplished by stirring the beads into a freshly prepared solution of four weight percent octadecyltrichlorosilane in warm ethanol for 3 – 4 minutes. They were subsequently washed with ethanol, dried, washed with distilled water and dried. Final hydrocarbon content was 3.29%.

Figure 2:
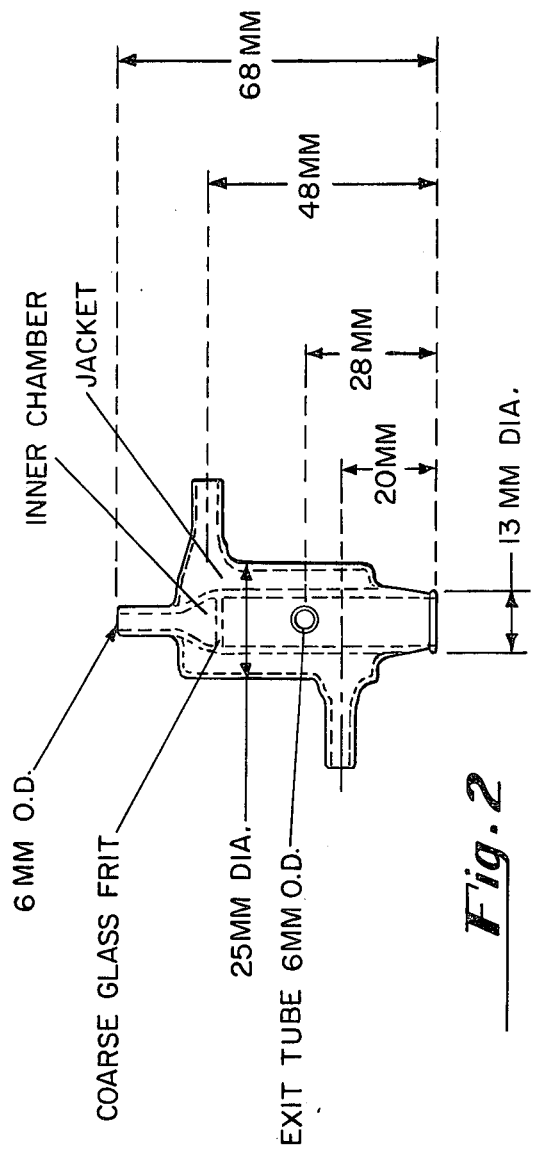
FIG. 2 is a sketch of apparatus used and referred to in Example I.

A charge of 0.35 gms of the treated beads was placed in a closed sample chamber. A Yellow Springs Instrument model 5331 Clarke type polarographic electrode covered with a 1 mil fluorinated ethylene-propylene copolymer film was inserted into the chamber. Measurements were made with the Yellow Springs Instrument's oxygen monitor. The total volume of the chamber up to the level of contact with the electrode was 0.6 ml. This apparatus design is shown in FIG. 2. Flow of solution to the apparatus was supplied by a syringe pump. Before reaching the apparatus, the solution passed through a heat exchanger of 7 ml volume packed with broken fritted glass—the packing was used to remove supersaturated air from solution. Both heat exchange and sample apparatus were maintained at 27.0° C. A 4 inch gum rubber tube connected the heat exchanger exit to the sample chamber inlet. Injections of mitochondria and reactants were made by piercing the rubber tubing with a 26 gauge needle.

Figure 3:
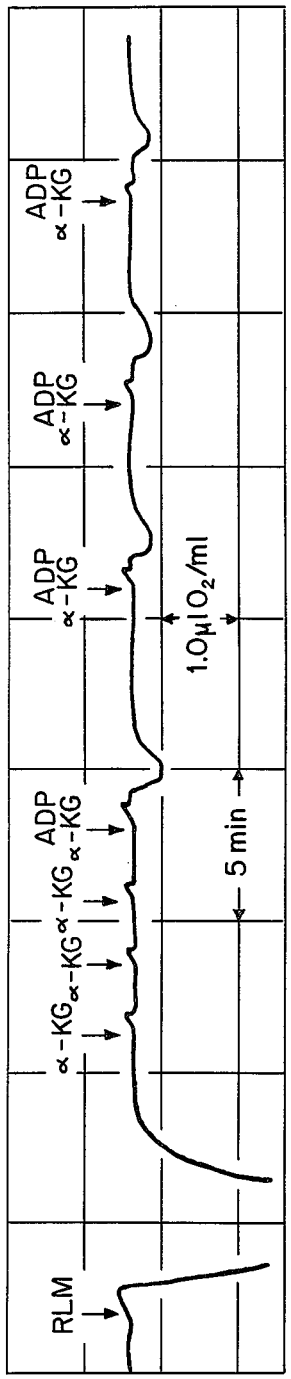
FIG. 3 is a chart showing the course of the reaction described and referred to in Example I.

A uniform flow of 0.25 M sucrose solution containing 5 mM potassium monobasic phosphate and 25 mM potassium chloride adjusted to pH 7.4 was established at 1.3 ml/minute. Approximately 0.4 ml of mitochondrial suspension was equilibrated at 27.0° C and then injected. In approximately 30 seconds a large drop in oxygen concentration was observed. The silica beads assumed a light yellow cast indicative of the mitochondria bound on the bead surface. After several minutes the oxygen concentration returned to a steady state. A simultaneous injection of ADP and α-ketoglutarate resulted in an increase in oxygen consumption to a maximum of 0.4 ml/min. Analysis of the effluent indicated presence of ATP demonstrating the net synthesis of ATP from ADP + Pi.* The course of the experiment is shown in FIG. 3.

*inorganic orthophosphate

EXAMPLE II

Sample and apparatus preparation was similar to Example I. Sucrose-$P_i$ solution containing a 5 mM α-ketoglutarate and 3 mM$^{++}$ was used at a flow rate of 3.0 ml/min. Upon return to a steady state after mitochondrial addition 10 μl of 6:0 mM ADP was injected into the stream. An uptake of 0.26 μl of oxygen was observed after one minute. Total ATP synthesized, measured using firefly luminescence, was 0.06 μ moles, i.e. essentially all the ADP was converted to ATP. The P:O ratio was 0.66/2(0.011) = 2.7, essentially the same as the traditional value obtained for mitochondria in suspension.

EXAMPLES III – VIII

Adhesion of mitochondria was demonstrated with a variety of lipophilic surfaces. In each case a yellow cast was observed on the beads after mitochondria were mixed with the porous silica beads. Optimum adhesion occurred when the hydrocarbon length was eight or greater.

Table I

| | AMOUNT OF MITOCHONDRIA BOUND AS A FUNCTION OF LENGTH OF HYDROCARBON CHAIN | | | |
|---|---|---|---|---|
| Example No. | Silane | Solution in Ethanol g/100 ml | Hydrocarbon on Beads g/100 g | Mitochondria, Dry Weight on Beads g/100 g |
| III | Ethyltrichlorosilane | 9 | 3.1 | 0.4 |
| IV | Butyltrichlorosilane | 8 | 2.7 | 0.4 |
| V | Octyltrichlorosilane | 6 | 3.5 | 0.9 |
| VI | Tetradecyltrichlorosilane | 5 | 3.2 | 1.4 |
| VII | Octadecyltrichlorosilane | 4 | 3.0 | 1.3 |
| VIII | Octadecyldimethyl [3-(trimethoxy 3-silyl)-propyl] ammonium chloride | 3 | 1.7 | 0.9 |

EXAMPLE IX

Microsomes were prepared from rat liver following the procedure in Example I. The supernatant, after the 9000xg sedimentation of mitochondria, was recentrifuged at 24,000xg and the supernatant consisting of crude microsomes was retained. The apparatus contained porous silica beads treated with octadecyltriethoxysilane to yield a hydrocarbon content of 2.7%. Upon injection of the microsomal suspension, the beads assumed a pale pinkish cast. Analysis indicated 0.7% bound microsomes.

EXAMPLE X

Active phosphorylating chloroplasts were isolated from spinach leaves by grinding 50 g of leaves in a precooled mortar with 100 ml of 0.35 M NaCl, 10 ml of 0.2 M Tris buffer at pH 8, and 50 g of cold sand. The slurry was squeezed through cheese cloth and centrifuged at 0° C for 1 minutes at 200xg. The supernatant was retained and centrifuged for 7 minutes at 1000xg. The supernatant was discarded and the pellet of chloroplasts resuspended in about 2 ml of 0.35 M NaCl. As described in Example 1 the chloroplasts were added to the alkylsilylated glass beads. The beads immediately assumed a green cast. Oxygen evolution was observed with the bound chloroplasts were exposed to intense light, indicating that the photosynthetic apparatus remained intact. No indication of any reduction an adhesion was observed over a temperature range of 0° – 30° C for a period of two weeks.

We claim:

1. Cellular organelles, from the group consisting of mitochondria, microsomes and chloroplasts, bound and immobilized in an active state on a substantially inert and insoluble solid substrate from the group consisting of glass, kaolin, talc, silica, ferrite, alumina and high molecular weight polymers.

2. Bound cellular organelles, as recited in claim 1, wherein said organelles are hydrophobically bound on said substrate.

3. Bound cellular organelles, as recited in claim 2, wherein said support includes a residue of an uncharged alkyl silane.

4. Bound cellular organelles, as recited in claim 2, wherein said support is in the form of beads in the range of 100 – 150 mesh.

5. Bound cellular organelles, as recited in claim 3, wherein said alkyl substituent of said silane includes from two to twenty-four carbon atoms.

6. Bound cellular organelles, as recited in claim 3, wherein said alkyl silane is of the general structure $R_nSiX_{4-n}$ where $n = 1$ to 3, X is a labile substituent selected from the group consisting of halogen and alkoxy, and R is hydrocarbon of 2 to 24 carbon atoms.

7. Bound cellular organelles, as recited in claim 1, wherein said organelles are mitochondria.

8. Bound cellular organelles, as recited in claim 1, wherein said organelles are chloroplasts.

9. Bound cellular organelles, as recited in claim 1, wherein said organelles are microsomes.

10. Bound cellular organelles, as recited in claim 2, wherein said support comprises porous silica beads.

11. A process for producing desired biological chemical substances by bringing reactive precursor chemical substances into contact with a bound organelle as recited in claim 1.

12. Method of binding sub-cellular organelles in an active state on an inert solid support comprising:
    (a) isolating organelles selected from the group consisting of mitochondria, microsomes and chloroplasts and removing substantially all excess lipid therefrom;
    (b) preparing an inert support from the group consisting of glass, kaolin, talc, silica, ferrite, alumina and high molecular weight polymers, by treating said surface with a hydrophobic coupling agent; and
    (c) contacting said prepared inert solid support material with said organelle, free of excess lipid, and permitting said support material and said organelles to remain in contact until a significant amount of said organelles are bound and immobilized on said substrate.

13. Method as recited in claim 12, wherein said hydrophobic coupling agent is an alkylsilane of the general structure $R_nSiX_{4-n}$ where $n = 1$ to 3, X is selected from the group consisting of halogen and alkoxy, and R is hydrocarbon of 2 to 24 carbon atoms.

* * * * *